United States Patent [19]

Rhee

[11] 4,300,543
[45] Nov. 17, 1981

[54] PROTECTIVE CAST DEVICE

[76] Inventor: Jhoon G. Rhee, 2000 L St., NW., Washington, D.C. 20036

[21] Appl. No.: 79,418

[22] Filed: Sep. 27, 1979

Related U.S. Application Data

[63] Continuation-in-part of Ser. No. 905,470, May 12, 1978, and a continuation-in-part of Ser. No. 941,946, Sep. 13, 1978, and a continuation-in-part of Ser. No. 26,519, Apr. 3, 1979.

[51] Int. Cl.³ .............................................. A61F 5/04
[52] U.S. Cl. .................................... 128/89 R; 128/90
[58] Field of Search .................... 128/87 R, 89 R, 90, 128/89 A

[56] References Cited

U.S. PATENT DOCUMENTS

| 2,878,153 | 3/1959 | Hackländer | 128/89 R |
| 3,117,786 | 1/1964 | Anderson | 128/89 R |
| 3,911,497 | 10/1975 | Lewis, Jr. et al. | 128/89 R |
| 4,190,902 | 3/1980 | Rhee | 128/87 R |

*Primary Examiner*—Robert W. Michell
*Assistant Examiner*—C. W. Shedd
*Attorney, Agent, or Firm*—James C. Wray

[57] ABSTRACT

This invention relates to protective cast devices for various parts of the body. The protective cast device of the present invention comprises a thin relatively rigid bendable lightweight closed cell member on which straps are fixed to form and hold the device about a body part. Once the device is bent and secured in one direction, it resists bending in any other direction. The member has a relatively more dense outer skin and a relatively less dense and more soft inner surface.

7 Claims, 5 Drawing Figures

PROTECTIVE CAST DEVICE

REFERENCE TO RELATED APPLICATIONS

This is a Continuation-in-Part of my co-pending applications Ser. Nos. 905,470, filed May 12, 1978, 941,946, filed Sept. 13, 1978, and 26,519, filed Apr. 3, 1979.

BACKGROUND OF THE INVENTION

This invention relates to protective cast devices adapted to be worn on various parts of a person's body. In particular, this invention relates to protective cast devices and the particular construction of those devices which may be used on fingers, thumbs, wrists, arms, elbows, necks, heads, backs, rib cages, abdomens, legs, knees, ankles, and feet. The cast devices of the present invention provide protection and support to various parts of the body and can be used in a number of different contact sports such as football, hockey, and the like.

The protective cast devices of the present invention are particularly useful as permanent protective splints for injured parts of the body to substantially immobilize the injured body parts during healing thereof. The devices of the invention are also useful as temporary protective splints to substantially immobilize injured body parts prior to medical treatment.

SUMMARY OF THE INVENTION

The protective cast devices of the present invention are constructed of planar sheet material. Preferably the sheet material is lightweight and is stiff. When the protective casts are bent around a body part, longitudinally relatively straight walls are formed which resist further bending. The walls are generally cylindrical in shape and in some cases are slightly inwardly tapered to conform to the shape of the body part which is surrounded. The devices can be economically produced, shipped, and stored. One device is adjustable and usable to fit a wide range of varied sizes of body parts. Preferably the devices are made and shipped and stored in flat configurations, and they are bent into curvilinear shapes immediately prior to their use. Alternatively, the devices may be constructed in flat configurations and may be subsequently bent into their general shape with several devices telescoped one into the other and at least the outermost device fastened by its own straps or by a separate holding strap into a shape which is generally similar to the desired conical shape. Alternatively the devices may be shipped in the flat state and the devices may be stored in the flat shape with a few of the devices preshaped into the conical shape before use. For example, a clinic may store many casts of the same type and maybe keep three casts of each type bent into a conical shape for emergency use.

Preferably the devices are made of a relatively stiff material which may be readily bent in a generally cylindrical shape. A non-memory material is preferred which tends not to retain its original shape but tends to retain its new shape when bent into the new generally cylindrical shape. Once bent in a curved shape about one axis, the material tends to resist bending in any other direction. A preferred material is a relatively stiff closed cell plastic foam material having a thickness of approximately ⅛" to ½", preferably about ¼ or ⅜ of an inch. The material is extremely lightweight. In a preferred embodiment, a self skin is formed on the outside of the material and the self skin is relatively more dense than the material of the remaining thickness. In one form of the invention a more soft lining is formed on the inner surface of the member. The more soft lining may be a relatively less dense closed cell plastic foam material. The material may be the same material with changing densities and characteristics in a transverse direction.

In a preferred form of the invention, holes may be provided for air circulation.

It is an object of this invention to provide novel unitary protective devices to be worn on various parts of a person's body such as fingers, thumbs, wrists, arms, elbows, necks, heads, backs, rib cages, abdomens, legs, knees, ankles, and feet while engaging in various sporting activities and to be worn as permanent or temporary splints or casts on injured body parts.

Another object of this invention is to provide novel protective cast devices of simplified construction which are relatively inexpensive and which will both aid in preventing injuries to parts of a person's body and which also will protect and support and immobilize injured body parts.

Another object of this invention is to provide novel protective cast devices of stiff bendable material which would, bent in a generally cylindrical form around one axis, resist bending in any other axis. The forms which the protective cast device may take are, for example, shown in co-pending application Ser. No. 26,519, filed Apr. 3, 1979.

An object of the invention is to provide a protective cast device adaptably to be worn around a part of a person's body, the device having a sheet-like planar contoured shape adapted to conform generally, substantially in the form of a cylinder, to the shape of the body part when said device is worn and secured around said body part, the device having a plastic foam member which, when curved in one direction, resists curving in any other direction and fastening means connected to the plastic foam member for maintaining the member curved in one direction around a body part whereby the member resists bending in any other direction.

Another object of the invention is the provision in a protective cast device a semi-rigid plastic foam member which is a closed cell foam member and a low density closed cell foam member.

Another object of the invention is the provision of a protective device of a semi-rigid closed cell member with an outer relatively more dense skin integrally formed on the member on a side thereof away from a body part around which the protective cast is bent.

The invention has as a further object the provision of a protective cast device wherein fastening straps are connected to relatively more dense outer skin of a foamed semi-rigid polymeric material.

Another object of the invention is the provision of a protective cast device having a relatively softer closed cell plastic foam material inward of the semi-rigid closed cell plastic material on a side thereof toward a body part around which the protective cast device is bent.

Another object of the invention is the provision of a protective cast device with a lightweight, thin semi-rigid member which tends to resist bending.

A further object of the invention is the provision of a protective cast device constructed on non-memory foam material which tends to retain its bent shape after being bent.

In a preferred embodiment semi-rigid low density closed cell polymeric foam is used in the protective cast devices of the present invention. The one-quarter inch, which is preferred, material has rigidity which is necessary for the protective cast device and also has a cushion effect. When more cushion effect is desired, the protective cast device is constructed of one-eighth inch semi-rigid closed cell foam material with an inner layer of one-eighth inch softer closed cell foam material.

As an example, Uniroyal AF material or a similar material may be used. A semi-rigid polypropylene foam is suitable.

These and further and other objects and features of the invention are apparent in the disclosure which includes the drawings and the specification consisting of the above and on-going written materials which include the claims.

DETAILED DESCRIPTION OF THE DRAWINGS

Figure 1:
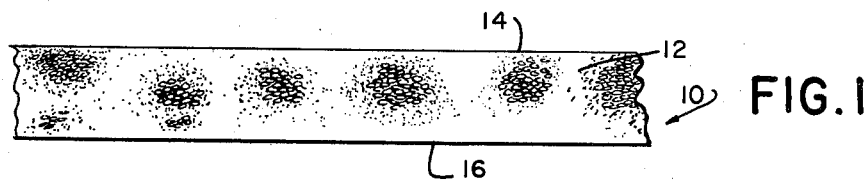
FIG. 1 is a cross-sectional detail of a protective cast device member made of a lightweight bendable and stiff closed cell foam plastic material.

Referring to the drawings, a preferred light stiff closed cell foam cast 10 uses the material 12 shown in FIG. 1. The closed cell foam plastic material extends uniformly from the outer surface 14 to the inner surface 16. Once the material is bent in a curve around one axis, it resists bending in another axis. Strap means, as later will be described, are added to an outer surface 14 of the material to form a cast device.

Figure 2:
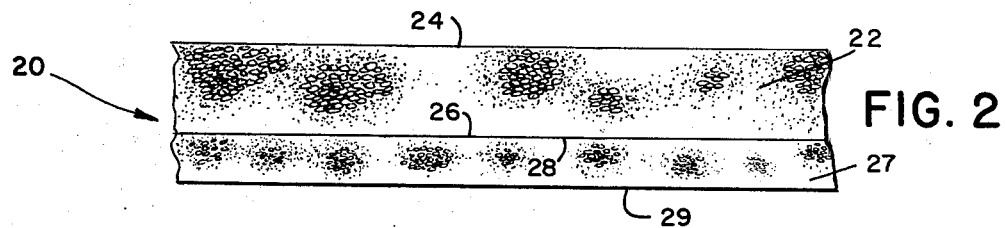
FIG. 2 shows the material of FIG. 1 on which a relatively softer and less dense material is formed on an inner surface which will be against the body part in use.

As shown in FIG. 2, a preferred form of the protective cast device 20 has a closed cell foam material 22 similar to material 12 in FIG. 1. The lightweight relatively stiff but bendable closed cell foam material 22 has an outer surface 24 and an inner surface 26. On the inner surface 26 an outer surface 28 of a relatively more soft and less dense closed cell foam material is bonded. The soft closed cell foam material 27 has an inner surface 29 which rests against the body part which the cast device 20 surrounds.

Preferably the cast devices 10 and 20 are constructed of a non-memory foam material which tends not to return to the original flat shape after the material is bent, but to retain the bent shape. With respect to the protective cast device 20, shown in FIG. 2, it is noted that the material 27 may be a contiguous material with a no interface 26 or 28 which is uniformly formed of varied density and softness with the outer portion of the cast material.

Figure 3:
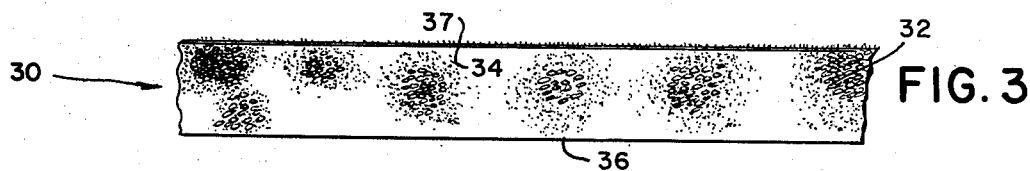
FIG. 3 shows the material of FIG. 1 in which a relatively more dense self skin on the outer surface.

Referring to FIG. 3 a protective cast device 30 is shown constructed of a closed cell foam material 32 similar to the closed cell foam material 12 shown in FIG. 1. The closed cell foam material has an inner surface 36 and has a skin 37 which may be referred to as a self skin directly formed on the outer surface 34. Self skin 37 is relatively more dense than the foam material 32. The self skin has two functions in that it tends to resist wear of the foam and resists gathering dirt and is easily cleaned. At the same time, the self skin is relatively less deformable than the inner material. The self skin may place the inner material 34 in greater compression and may create greater rigidity in the curved member than in other forms of the invention without the self skin.

Figure 4:
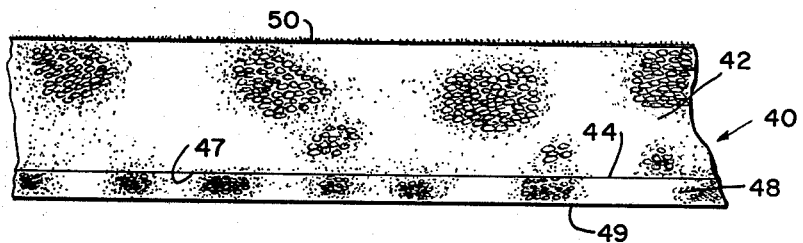
FIG. 4 shows the material of FIG. 3 in which a relatively softer and less dense material is formed on the inside.

In FIG. 4 there is shown a protective cast device 40 which has a closed cell foam material 42 similar to material 32 shown in FIG. 3. A self skin 50 is formed on the outer surface 42. A relatively less dense and softer closed cell foam plastic material 48 has an outer surface 47 which is bonded or integrally joined with inner surface 44 of the relatively more rigid material 42. The inner surface 49 of material 48 contacts the body part with greater comfort than the relatively more rigid material 32 as shown in FIG. 3.

Figure 5:
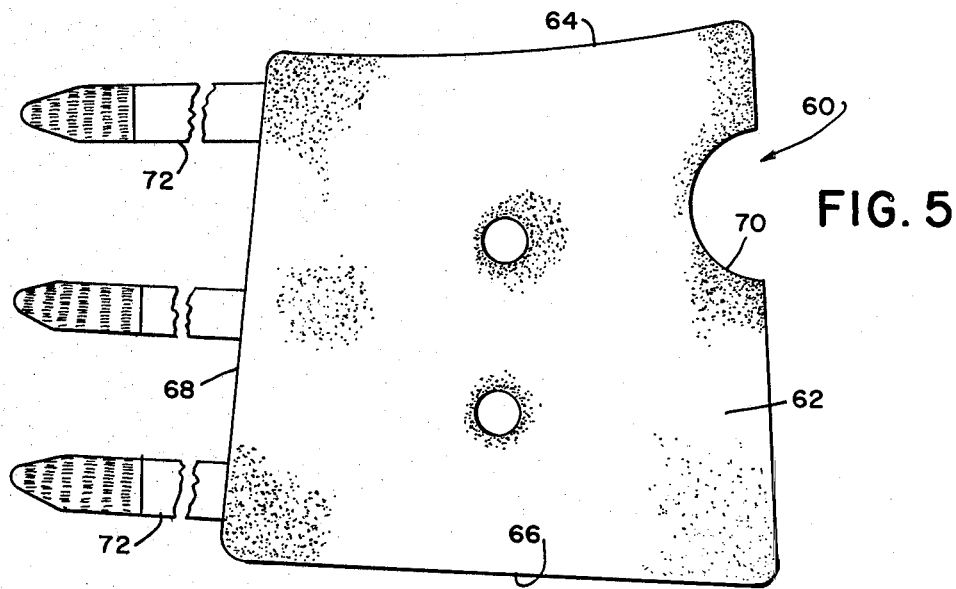
FIG. 5 is an example of a protective cast device which employs the material of FIGS. 1-4.

As shown in FIG. 5, in one example of an entire protective cast device 60 the device is made of a generally rectangular sheet of closed cell plastic material 62.

One edge 64 of the protective cast device 60 is slightly curved to fit the desired contour of the body. The opposite edge 66 may be curved or relatively straight. Side edges 68 may diverge in the case of protective cast devices which are slightly conical. A cutout portion 70 may be provided as is necessary to fit particular body parts. In the example shown the cutout 70 and the curve edge 64 are provided to surround a wrist area of a user with the edge 64 overlying the back of the hand and the cutout portion 70 partially encircling a thumb.

Straps 72 have one element of miniature hook and loop-type fasteners, for example, loops which engage complementary fasteners, for example miniature hooks in strips fastened to an opposite outer surface.

The particular cast and the strap means may be of several configurations for different body parts. For example, the configurations shown in the co-pending patent applications.

Once the protective cast device 60 is curved around an axis transverse to the direction of the straps with the body member interposed and the straps are closed, the protective cast device resists bending in any other direction.

Apertures as shown centrally in a cast, in FIG. 5, are provided throughout the surface of the cast to provide adequate circulation.

The protective cast device of the present invention has many applications. For example, fire and rescue squads, emergency medical teams, sports trainers, and ski-patrols, military corpsmen, and medics, orthopedic surgeons, and physical therapists have many uses for the protective casts of the present invention.

Patients with healing fractures can be out of plaster casts in a few weeks and into the present protective body cast for the remaining healing period. The patient can bathe the injured area helping to minimize skin problems experienced with long term permanent cast.

A cast of the present invention can be applied in a few seconds and there is no need to sterilize materials. The closed cell foam is a firm, active material which can be readily adjusted to the needs and comfort of the wearer. Movement can be completely or partially restricted while maintaining integrity of the protective cast device.

While the invention has been described with reference to specific embodiments, it will be obvious that other embodiments and modifications may be constructed without departing from the scope of the invention which is defined in the following claims.

I claim:

1. A protective cast device adaptably to be worn around a part of a person's body, said device having a sheet-like planar contoured shape adapted to conform generally, substantially in the form of a cylinder, to the shape of the body part when said device is worn and secured around said body part, said device comprising a lightweight, thin, relatively stiff non-memory plastic foam material member which tends to resist bending, which tends to retain its bent shape after being bent and which, when curved in one direction, resists curving in any other direction and fastening means connected to the plastic foam member for maintaining the member curved in one direction around a body part whereby the member resists bending in any other direction.

2. The protective cast device of claim 1 wherein the plastic foam member comprises a closed cell foam member.

3. The protective cast device of claim 2 wherein the closed cell foam member comprises a low density closed cell foam member.

4. The protective cast device of claim 2 wherein the closed cell foam member has an outer relatively more dense self skin formed on the member on a side thereof away from a body part around which the protective cast is bent.

5. The protective cast device of claim 4 wherein the fastening means comprise strap means connected to the relatively more dense outer skin.

6. The protective cast device apparatus of claim 4 further comprising a relatively less dense closed cell plastic foam material connected inwardly of the closed cell foam member on a side thereof toward the body part around which the protective cast device is bent.

7. The apparatus of claim 2 further comprising a relatively less dense closed cell plastic foam material on a side of the closed cell foam member facing the body part around which the protective cast is bent.

* * * * *